United States Patent [19]

Persoons

[11] Patent Number: 5,683,460
[45] Date of Patent: Nov. 4, 1997

[54] INTRAFOCAL PEG AND METHOD OF REPAIRING FRACTURE

[76] Inventor: Dominique Persoons, 16, les Maisons dans la Colline, F-62150 Rebreuve-Ranchicourt, France

[21] Appl. No.: 576,503

[22] Filed: Dec. 21, 1995

[30] Foreign Application Priority Data

Mar. 8, 1995 [WO] WIPO ............. PCT/BE95/00072

[51] Int. Cl.6 ............................ A61F 2/30; A61F 2/42
[52] U.S. Cl. .................... 623/16; 623/21; 606/60; 606/72; 606/73
[58] Field of Search ......................... 623/16, 18, 21; 606/60, 62, 72, 73, 74; 433/173, 174

[56] References Cited

U.S. PATENT DOCUMENTS

| | | |
|---|---|---|
| 4,969,888 | 11/1990 | Scholten et al. |
| 5,006,120 | 4/1991 | Carter . |
| 5,129,904 | 7/1992 | Illi ................................ 606/72 |

OTHER PUBLICATIONS

A. Kapandji, May 5, 1986: *L'Embrochage Intra–Focal Des Fractures De L'extrémité Inférieure Du Radius Dix Ans Aprés.*

Primary Examiner—John G. Weiss
Assistant Examiner—John M. Black
Attorney, Agent, or Firm—Barnes & Thornburg

[57] ABSTRACT

An intrafocal peg includes a body having a first end and a second end. The first end has a greater cross-sectional area than the second end. A blocking member is provided on the peg. The blocking member may take the form of a helical thread or a plurality of unconnected protruding members. The blocking member defines one or two notches. The peg is inserted into the fracture such that the posterior cortical wall of the metaphysis of the radius is located in a notch formed by segments of the blocking member at the first end of the peg. Blocking members may also be provided at the opposite end of the peg to form a second notch in which the anterior cortical wall or the metaphysis of the radius is located.

3 Claims, 1 Drawing Sheet

5,683,460

INTRAFOCAL PEG AND METHOD OF REPAIRING FRACTURE

BACKGROUND AND SUMMARY OF THE INVENTION

The present invention relates to an intrafocal peg for stabilization and osteosynthesis of a fracture of the wrist, particularly with a defect of cortical bone at the postero-lateral part of the metaphysis of the radius.

Osteosynthesis of the wrist fracture known as PouteauColles or Colles remains difficult. Colles fractures of the wrist are common by old people. Indeed, in an osteoporotic bone, fracture induces a collapse of the posterior and lateral sides of the radial distal metaphysis. The bone defect appears secondary to the reduction and must be compensated, since the reduction of the displacement does not restore the bone integrity. If not compensated, there is a great chance of re-displacement of the fracture, even under protection of a cast or POP.

Four surgical procedures are, so far, commonly used:
bone grafting under protection of an external fixator;
distracting (re-opening) the fracture by using oblique wires (Kapandji);
elastic osteosynthesis with long wires; and
static synthesis with plate and screws.

These solutions have, however, inconveniences: the pegs or wires are flush and can cause skin or tendon troubles; the elastic wires or pegs are sometimes unstable; the external fasteners give rise to stiffness; and the treatment by bone graft is too heavy for a fracture which is very common by old people.

An object of the invention is thus to provide means for allowing a rapid and slightly invading treatment, which first aims at obtaining a stable reduction by compensating the loss of bone substance on the external posterior side of the radius.

This and other objects of the present invention are attained by an intrafocal peg and method of use according to the invention. The peg includes a body which has, at a first end, a larger cross section than at its second end, and includes a blocking member defining, at least at the first end, between substantially radially protruding first and second sequential members, a first notch intended for housing the posterior cortical wall of the metaphysis of the radius. The section of the first end of the body is intended for substantially compensating the bone defect at the postero-external side of the metaphysis of the radius. This peg is introduced into the focus of the fracture to re-open it, and it passes through the entire width of the radius to stabilize at least its posterior cortical wall, and preferably also the anterior cortical wall.

According to other characteristic features of the peg of the invention, the blocking member additionally includes third and fourth substantially radially protruding sequential members at the second end of the body defining a second notch intended for housing the anterior cortical wall of the metaphysis of the radius. The protruding members may be individual members, each surrounding at least part of a section of the body. The body may include at the first end a head with a larger section than the first end, and constituting the first protruding member. A terminal part of some protruding members of the blocking member can be disposed at an angle relative to the longitudinal axis of the body. The blocking member may helically surround the body, and may extend substantially over the full length of the body, for housing the cortical wall at the posterior and anterior parts of the radius at the first and at the second ends of the body, respectively. The free space between two sequential turns of the blocking member forms the notches. The edges of the blocking member may be non-cutting and the base of the body may be a non-perforating, blunt or flat base. Also, the external face of the head can be rounded. The body of the peg may be hollow. The first protruding member may be angularly movable relative to the body.

Screws are known in surgery for performing fixation in a bone tissue. These screws are intended for entering forcibly into the bone, by gripping therein with their helical thread with a cutting edge.

In one embodiment, the peg of the invention has an external appearance which is somewhat similar to such a screw, with an elongated body and an helical thread. It includes, however, features, and performs functions essentially different, particularly in that it performs no penetration function in the bone, but rather slips between two pieces of bone, and in that it also performs by itself no fixation of the bone pieces, as a screw would do, but rather acts as a wedge pushing away the bone pieces pressed together by the muscles and the tendons.

In addition to its wedging effect, obtained by a longitudinal flaring of its body, the peg also stabilizes laterally the fracture by fixing the cortical wall of the broken bone, on each side of the fracture, and preferably at the anterior face as well as at the posterior face of the radius, due to the notching effect of peripheral protrusions.

In the method, the Colles fracture is first reduced. Then, according to the invention, the fracture site is checked under image intensifier. A skin incision is made at the posterior or lateral side of the metaphysis of the radius, in front of the fracture line. A thin forceps is introduced between the tendons, in the bone defect itself, and then pushed straight away up to beyond the opposite cortex, through the fracture at the opposite cortex, under X-ray control. In front of the anterior cortex, care is taken not to damage the medial nerve and noble structures. The depth is measured and the forceps removed. The peg is driven along the same direction, so that 2 to 3 mm protrudes from the anterior cortex and the base of the head abuts the posterior cortex. The thread blocks or holds the peg in the fracture site, between the fragments of the anterior cortex and between those of the posterior cortex. A secondary peg may be added with the same technique or simplified procedure without fixation on the opposite cortex. The forceps checks that no tendon is jammed and the skin is closed. A Plaster of Paris (POP) or a frame is recommended for a 4 week-period.

As it can be understood from the above, the peg is introduced within the fracture where it takes the place of the bone defect in the posterior or lateral cortex of the radial metaphysis. It seems better that the peg be inserted also between the fragments of the anterior or medial cortex, in order to better stabilize the peg. No bone replacement is however aimed at the anterior and medial cortex. To prevent secondary displacement, blocking means is provided at least at one end part of the peg.

Other objects, advantages and novel features of the present invention will now become apparent from the following drawings and detailed description of the preferred embodiments.

DETAILED DESCRIPTION OF THE PREFERRED EMBODIMENTS

Figure 1:
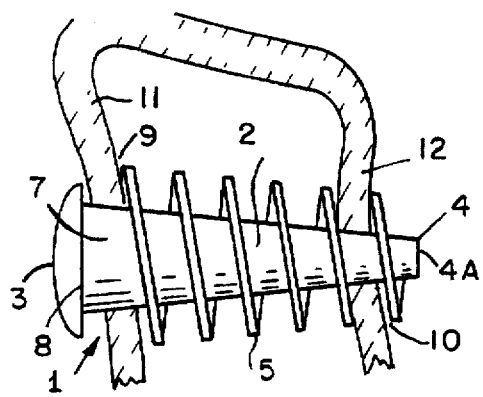
FIG. 1 is a side plan view of an embodiment of an intrafocal peg according to the present invention inserted in a fractured bone.

Referring to FIG. 1, the peg 1 includes a body 2 having at one end 8 a head 3, and including at the opposite end 4 a non-perforating, blunt or flat base 4A. Body 2 bears a blocking member in the form of a helical thread 5 protruding radially from body 2. Thread 5 has a non-cutting, blunt or flat edge. The head 3 is separated from the collar 7 by a steep edge, while the generating line of the helical thread 5 is substantially perpendicular to the longitudinal axis of the body 2. The thread 5 ends at a distance from the head 3 leaving a collar part 7 of the body adjacent head 3. The terminal edge of thread 5 is blunt near base 4A and at the opposite end 8 to avoid damaging the tissues.

FIG. 1 also shows part of the radius in cross section to illustrate the use of the peg 1. The posterior cortical wall 11 is housed within a notch 9 formed between the head 3 and the terminal turn of the thread 5. The anterior cortical wall 12 is housed within a notch 10 formed between two sequential turns of thread 5 near end 4 of peg 1.

The diameter of the body at the collar 7 is greater than its diameter at base 4A for performing a wedging effect so as to open the focus of the fracture and compensate for the defect of cortical bone at the postero-external face of the radius (at the head side of the peg 1).

The external face of the head 3 is rounded and smooth, in order to avoid damage to the neighboring tissue. The base 4A is also not pointed for the same reasons; the base need not be pointed, since the peg is intended to be inserted at the focus of the fracture and so does not need to be perforating. Also, the edge of the helical thread 5 is non-cutting, to avoid damage to the tissue, while the pitch of the helical thread 5 is such that the free space between two turns is appropriate for housing the cortical wall of the radius.

The collar section 7 compensates for the bone defect due to the collapse of the posterior cortical wall 11, and allows the unfolding of the posterior face of the focus of the fracture.

On fracturing, the anterior cortical wall 12 is, on the other hand, not subject to collapse, so that the diameter of the body 2 of the peg 1 at end 4 may be as little as possible, taking account for the fact that it must still have a section sufficient for assuring a non-damaging contact with the neighboring tissue.

The section of the body 2 between the collar 7 and the base 4 plays no role when the peg is set in place. Preferably, however, the body 2 will be flared uniformly in the longitudinal direction, in order to provide for a progressive diverting, and thus a constant force, of the focus of the fracture, when the peg 1 goes farther through the radius. The intrafocal peg 1 according to the invention may be hollow, to be guided by a guide-peg.

The peg 1 will be inserted in place from the posterior face of the radius, by rotation like a screw, with for example the aid of a tool similar to a screwdriver, cooperating with a recess provided in the head 3, the thread 5 assisting the insertion of the peg by gripping on the cortical wall of the bone.

Several alternative embodiments are described below. In each case, a multiple of 100 has been added to the reference numbers of FIG. 1 to show corresponding elements.

Figure 2:
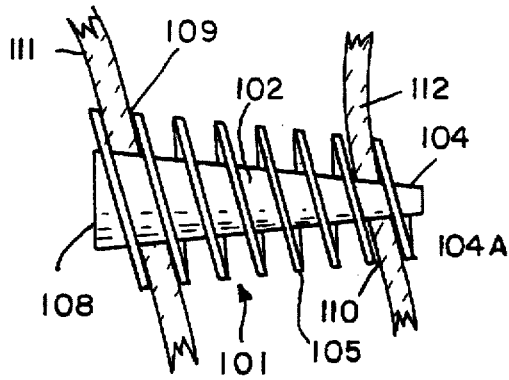
FIG. 2 is a side plan view of another embodiment of an intrafocal peg according to the present invention inserted in a fractured bone.

In the alternative embodiment of FIG. 2, the peg 101 does not include a head. The posterior cortical wall 111 is housed between the last two turns of thread 105, at end 108. The same is true of the cortical wall 112 at the base side 104.

Figure 3:
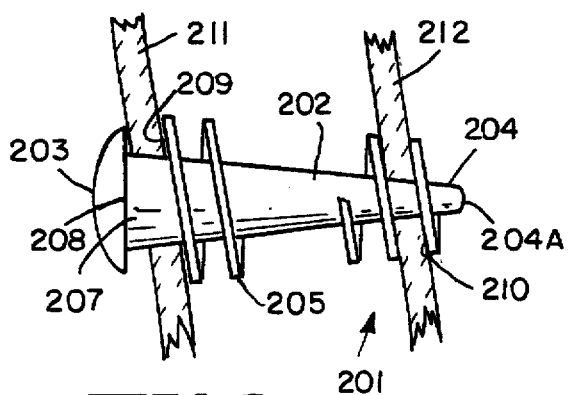
FIG. 3 is a side plan view of another embodiment of an intrafocal peg according to the present invention.

In the alternative embodiment of FIG. 3, the thread 205 is interrupted in the central part of the peg 201. Indeed, only the terminal parts of the thread 205 are used for blocking the cortical walls. The central part of the thread 205 is not used, and so may be omitted.

Figure 4:
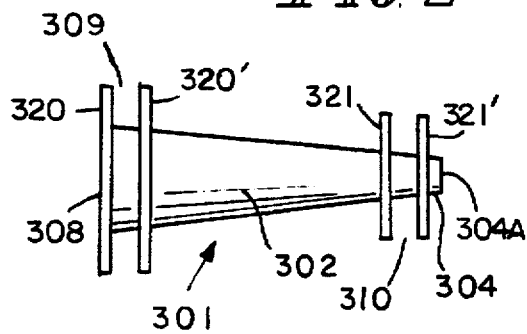
FIG. 4 is a side plan view of another embodiment of an intrafocal peg according to the present invention.

In the alternative embodiment of the FIG. 4, the blocking member takes the form of two sets of two adjacent radial protrusions 320, 320' and 321, 321' on the substantially conical body 302 at each end thereof. The protrusions 320, 320' and 321, 321' define notches 309 and 310 for housing the cortical wall at each face of the radius. Because the distance is fixed between the two notches 309 and 310, the peg 301 cannot be adjusted according to the size of the radius of the patient.

Figure 5:
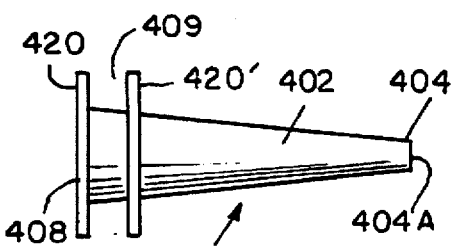
FIG. 5 is a side plan view of another embodiment of an intrafocal peg according to the present invention.

In the alternative embodiment of FIG. 5, only two protrusions 420, 420', defining a single notch 409, are provided. Indeed, although it is useful for better distributing the mechanical stress, it is not necessary to house the cortical wall at both sides of the radius. It is only necessary that the bone defect at the posterior face is compensated and that the two pieces of the broken bone are blocked against a lateral displacement. This is done by the peg shown in FIG. 5.

Figure 6:
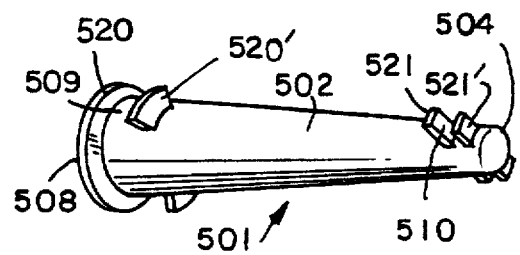
FIG. 6 is a perspective view of another embodiment of an intrafocal peg according to the present invention.
Figure 7:
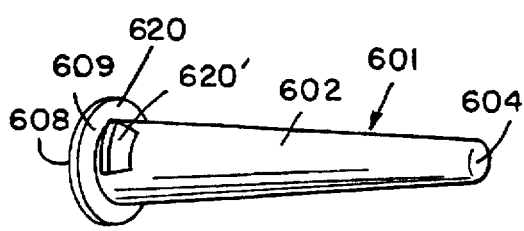
FIG. 7 is a perspective view of another embodiment of an intrafocal peg according to the present invention.

FIGS. 6 and 7 show alternative embodiments corresponding to the embodiments of FIGS. 4 and 5, respectively. In these embodiments, the protrusions 520, 520', 521, 521' and 620, 620' defining the notches 509, 510 and 609 for housing the cortical walls do not completely surround the body, but on the contrary, have a limited peripheral extension, facilitating placement of the peg, which may be inserted with the protrusions 520, 520', 521, 521' and 620, 621' substantially parallel to the fracture. The peg is thereafter pivoted by 90° for blocking, like a bayonet joint.

The discontinuous protruding members 520, 520', 521, 521' and 620, 620', or at least their terminal part, may be inclined along an acute angle to the longitudinal axis of the peg (like a helical thread 5), for facilitating passage beyond the cortical wall.

In the alternative embodiments of FIGS. 6 and 7, the protrusions 520 and 620 have been kept continuous for providing maximum support to the damaged cortical wall at the posterior part of the radius. It could, however, extend only on part of the periphery, like the protrusion 520' or 620'.

Figure 8:
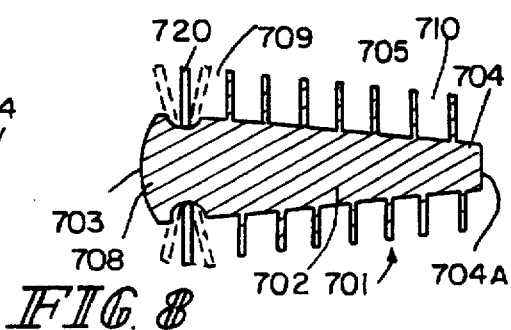
FIG. 8 is a cross-sectional view of another embodiment of an intrafocal peg according to the present invention.

In the embodiment of FIG. 8, the protruding member 720 is movable for allowing it to adjust to the inclination of the cortical wall (both terminal positions being illustrated by dotted lines).

As a another alternative embodiment, the part of the thread 205 on the base side 204 could also be omitted in the embodiment of FIG. 3 to obtain an embodiment analogous to the one of FIGS. 5 and 7.

Finally, in the embodiments of FIGS. 4 to 7, one could provide the various protrusions not perpendicular to the axis of the body of the peg, but obliquely relative thereto, so as to assist the insertion.

As regards the dimensions of the peg, they must be adapted to the size of the fractured radius. As an example, one may however mention the following dimensions:

head-collar step or shoulder: 9.5±1.5 mm (diameter or width)

diameter of the collar: 6.5±1.5 mm length of the body: 26±6 mm diameter of the base: 2.5±1.5 mm height of the thread: 2.2±1.2 mm Needless to say, the invention is not limited to the embodiments illustrated and described, which have been selected only as non-limitative examples.

What is claimed is:

1. A method for stabilization and osteosynthesis of a fracture of the wrist, comprising the steps of providing an intrafocal peg having a body with a first end, a second end and a blocking member defining at least one notch at the first end, wherein the cross section of the peg is larger at the first end than at the second end, and inserting the peg into the fracture, so that said larger cross section at the first end substantially compensates the bone defect at the postero-external side of the metaphysis, and the peg is secured to the posterior cortex by placing the cortical wall of the metaphysis of the radius within the notch.

2. The method according to claim 1, comprising the further step of inserting the peg into the fracture until the second end protrudes from the anterior cortex.

3. The method according to claim 2, wherein the blocking member defines a second notch at the second end, and comprising the further step of inserting the peg within the fracture until the anterior cortex is accommodated within the second notch.

* * * * *